United States Patent
Prater et al.

(10) Patent No.: US 9,687,210 B2
(45) Date of Patent: Jun. 27, 2017

(54) HIGH VOLUME RATE 3D ULTRASONIC DIAGNOSTIC IMAGING OF THE HEART

(75) Inventors: David Prater, Andover, MA (US);
Stephen Watkins, Windham, NH (US);
William Robert Martin, Westford, MA (US)

(73) Assignee: KONINKLIJKE PHILIPES ELECTRONICS N.V., Eindhoven (NL)

( * ) Notice: Subject to any disclaimer, the term of this patent is extended or adjusted under 35 U.S.C. 154(b) by 330 days.

(21) Appl. No.: 13/699,149

(22) PCT Filed: Apr. 25, 2011

(86) PCT No.: PCT/IB2011/051785
§ 371 (c)(1),
(2), (4) Date: Nov. 20, 2012

(87) PCT Pub. No.: WO2011/148275
PCT Pub. Date: Dec. 1, 2011

(65) Prior Publication Data
US 2013/0066207 A1    Mar. 14, 2013

Related U.S. Application Data

(60) Provisional application No. 61/348,313, filed on May 26, 2010.

(51) Int. Cl.
*A61B 8/00* (2006.01)
*A61B 8/08* (2006.01)
(Continued)

(52) U.S. Cl.
CPC ............. *A61B 8/0883* (2013.01); *A61B 8/08* (2013.01); *A61B 8/145* (2013.01); *A61B 8/4483* (2013.01);
(Continued)

(58) Field of Classification Search
CPC ........................................................ A61B 8/00
(Continued)

(56) References Cited

U.S. PATENT DOCUMENTS

| 4,958,226 A * | 9/1990 | Haskell et al. ........... 375/240.12 |
| 5,623,928 A | 4/1997 | Wright et al. |

(Continued)

FOREIGN PATENT DOCUMENTS

| JP | 2004160156 A | 6/2004 |
| JP | 2008079885 A | 4/2008 |

(Continued)

*Primary Examiner* — Tse Chen
*Assistant Examiner* — Lisa Kinnard

(57) ABSTRACT

A 3D ultrasonic diagnostic imaging system produces 3D cardiac images at a 3D frame rate of display which is equal to the acquisition rate of a 3D image dataset. The volumetric cardiac region being imaged is sparsely sub-sampled by separated scanning beams. Spatial locations between the beams are filled in with interpolated values or interleaved with acquired data values from other 3D scanning intervals depending upon the existence of motion in the image field. A plurality of different beam scanning patterns are used, different ones of which have different spatial locations where beams are located and beams are omitted. A sequence of different beam scanline patterns may be continuously repeated, or the patterns of the sequence synchronized with the cardiac phases such that, over a sequence of N heartbeats, the same respective phase is scanned by N different scanline patterns.

12 Claims, 4 Drawing Sheets

(51) Int. Cl.
  *G01S 7/52* (2006.01)
  *G01S 15/89* (2006.01)
  *A61B 8/14* (2006.01)

(52) U.S. Cl.
  CPC .............. *A61B 8/463* (2013.01); *A61B 8/483* (2013.01); *A61B 8/5253* (2013.01); *G01S 7/5208* (2013.01); *G01S 7/52034* (2013.01); *G01S 7/52087* (2013.01); *G01S 7/52092* (2013.01); *G01S 7/52095* (2013.01); *G01S 15/8915* (2013.01); *G01S 15/8925* (2013.01); *G01S 15/8993* (2013.01); *A61B 8/543* (2013.01)

(58) Field of Classification Search
  USPC ........................................................ 600/440
  See application file for complete search history.

(56) References Cited

U.S. PATENT DOCUMENTS

| | | | |
|---|---|---|---|
| 5,720,291 A | 2/1998 | Schwartz | |
| 5,993,390 A | 11/1999 | Savord et al. | |
| 5,997,479 A | 12/1999 | Savord et al. | |
| 6,013,032 A | 1/2000 | Savord | |
| 6,368,281 B1 | 4/2002 | Solomon et al. | |
| 6,419,633 B1 | 7/2002 | Robinson et al. | |
| 6,443,896 B1 | 9/2002 | Detmer | |
| 6,468,216 B1 | 10/2002 | Powers et al. | |
| 6,482,157 B2 | 11/2002 | Robinson | |
| 6,508,770 B1 | 1/2003 | Cai | |
| 6,544,175 B1* | 4/2003 | Newman | A61B 8/00 600/437 |
| 6,716,174 B1* | 4/2004 | Li | 600/447 |
| 7,537,567 B2 | 5/2009 | Jago et al. | |
| 2002/0143253 A1 | 10/2002 | Robinson | |
| 2005/0131298 A1 | 6/2005 | Cai | |
| 2006/0074310 A1 | 4/2006 | Thiele | |
| 2006/0241452 A1* | 10/2006 | Cerofolini | A61B 8/14 600/444 |
| 2007/0123110 A1 | 5/2007 | Schwartz | |
| 2007/0239001 A1* | 10/2007 | Mehi et al. | 600/437 |
| 2008/0175440 A1* | 7/2008 | Burns | H04N 7/014 382/107 |
| 2008/0252721 A1* | 10/2008 | Suzuki | 348/97 |
| 2009/0149756 A1 | 6/2009 | Soler et al. | |
| 2009/0156937 A1* | 6/2009 | Sasaki et al. | 600/447 |
| 2011/0125017 A1* | 5/2011 | Ramamurthy | A61B 8/08 600/443 |

FOREIGN PATENT DOCUMENTS

| | | |
|---|---|---|
| JP | 2009225948 A | 10/2009 |
| WO | 0217297 A1 | 2/2002 |
| WO | WO 2007148279 A1 * | 12/2007 |

\* cited by examiner

HIGH VOLUME RATE 3D ULTRASONIC DIAGNOSTIC IMAGING OF THE HEART

This invention relates to medical diagnostic ultrasound systems and, in particular, to ultrasound systems which perform real time 3D imaging of the heart at a high frame rate of display.

Ultrasonic imaging has been used for many years to scan and display two-dimensional (2D) image planes of the body in real time. In recent years real time 3D imaging has made its commercial appearance with the advent of matrix transducer arrays, ultrasound probes which use 2D transducer arrays to electronically scan a volumetric region of the body. An impediment to real time 3D imaging is the time required to scan a volumetric region. A typical 2D image plane can be scanned with 128 transmit and receive scanlines to form a 2D image. Even at the greatest diagnostic depths, the speed at which the ultrasound travels in the body, nominally 1580 meters/sec., enables images to be acquired rapidly enough for real time imaging. Real time imaging is generally a frame rate of display in excess of 20 frames per second, and preferably at least 30 frames per second, the frame rate of a standard NTSC television or display monitor. Scanning a volumetric region with the same scanline density, however, takes considerably longer, as the number of scanlines to be transmitted and received numbers in the thousands. The time to acquire a single 3D volumetric image is thus limited by the speed of sound at which the ultrasound pulses and echoes travel. The problem is compounded further when a moving organ such as the heart is images, since a long acquisition time can result in a blurred or distorted image, and becomes even more difficult with Doppler imaging, when each scanline must be pulsed multiple times. One of the few tradeoffs used to approach real time imaging is to only scan and image small volumetric regions. This will limit the field of view and hence the utility of diagnostic 3D ultrasound, however.

Another approach to live 3D ultrasound imaging is described in U.S. Pat. No. 5,993,390 (Savord et al.) In this approach a large field of view is divided into several volume segments. Each volume segment is separately imaged, then the image segments joined together to form a contiguous 3D image with a wide field of view. FIG. 5 of this patent gives an example for cardiac imaging. An image field for the heart is divided into nine volume segments. Each segment is imaged at each phase of the cardiac cycle. It takes nine heartbeats to acquire all of the necessary volume segments. Segments corresponding to the same phase are joined together, then the phase sequence of joined volumes is replayed at a real time rate of display, showing a live sequence of a large view of the heart beating for a complete heart cycle. While the resultant image sequence is live, it is not real time as the live image sequence is only available after the number of heartbeats needed to acquire the component volume segments.

Accordingly, it would be desirable to be able to ultrasonically image large fields of view in three dimensions and in real time. Furthermore, it would be desirable to do real time 3D ultrasonic imaging of organs of the body like the heart which are in motion, and to do so at a volume frame rate of display which is high enough to display the motion smoothly and without blurring, distortion, or other image artifacts.

In accordance with the principles of the present invention, a diagnostic ultrasound system is described which acquires volume image data for 3D images by sub-sampling the volumetric region with a low (widely spaced) scanline density that is sufficient to sub-sample the entire volumetric region in a time interval sufficient for a desired volumetric frame rate of display. Since the resultant image dataset can inadequately spatially sample the volumetric region, the image data is interpolated in the azimuth and elevation dimensions to fill in the spaces between acquired scanlines with interpolated image data. In a preferred implementation a plurality of different scan patterns are employed for different volume acquisitions of the heart. A sequence of different scan patterns can be continuously repeated, or the sequence of different scan patterns can be changed each heart cycle such that, over a plurality of heart cycles, each phase of the heart is sequentially scanned with each scan pattern. The image data of each volume acquisition may be interpolated to present an image consisting of acquired and interpolated image data, or some or all of the image locations which were not scanned can be filled in (interleaved) with acquired data from one or more other volume acquisitions. Preferably the decision to use interpolated or interleaved image data is made in real time and on a local, pixel-by-pixel basis.

In the drawings:

FIG. 4a illustrates four sub-sampling beam patterns in accordance with the present invention.

FIG. 4b illustrates the interpolation of image data at unsampled points of a volumetric region.

FIGS. 5a and 5b illustrate two sequences of sub-sampling beam patterns which may be used for cardiac imaging in accordance with the principles of the present invention.

FIG. 6 illustrates the sub-sampling of a volumetric region with a multiline beamformer.

Figure 1:
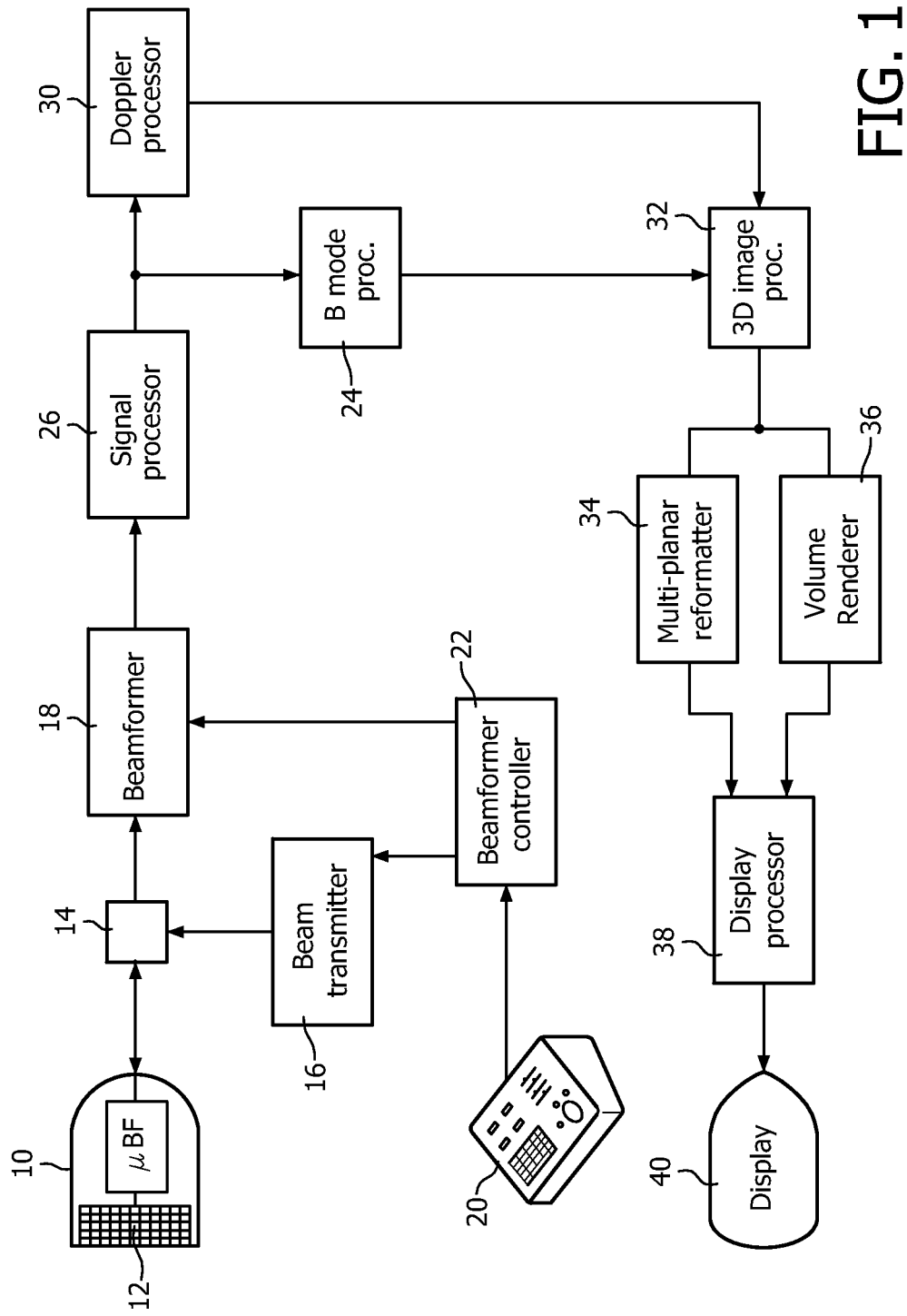
FIG. 1 illustrates in block diagram form a 3D ultrasonic imaging system constructed in accordance with the principles of the present invention.

Referring first to FIG. 1, an ultrasound probe 10 capable of three dimensional imaging includes a two dimensional array transducer 12 which transmits electronically steered and focused beams over a volumetric region and receives single or multiple receive beams in response to each transmit beam. Groups of adjacent transducer elements referred to as "patches" or "subarrays" are integrally operated by a microbeamformer (μBF) in the probe 12, which performs partial beamforming of received echo signals and thereby reduces the number of conductors in the cable between the probe and the main system. Suitable two dimensional arrays are described in U.S. Pat. No. 6,419,633 (Robinson et al.) and in U.S. Pat. No. 6,368,281 (Solomon et al.) Microbeamformers are described in U.S. Pat. No. 5,997,479 (Savord et al.) and U.S. Pat. No. 6,013,032 (Savord). The transmit beam characteristics of the array are controlled by a beam transmitter 16, which causes the apodized aperture elements of the array to emit a focused beam of the desired breadth in a desired direction through a volumetric region of the body. Transmit pulses are coupled from the beam transmitter 16 to the elements of the array by means of a transmit/receive switch 14. The echo signals received by the array elements and microbeamformer in response to a transmit beam are coupled to a system beamformer 18, where the partially beamformed echo signals from the microbeamformer are processed to form fully beamformed single or multiple receive beams in response to a transmit beam. A suitable beamformer for this purpose is described in the aforementioned Savord '032 patent.

The receive beams formed by the beamformer 18 are coupled to a signal processor which performs functions such as filtering and quadrature demodulation. The echo signals of the processed receive beams are coupled to a Doppler processor 30 and/or a B mode processor 24. The Doppler processor 30 processes the echo information into Doppler power or velocity information. For B mode imaging the receive beam echoes are envelope detected and the signals logarithmically compressed to a suitable dynamic range by the B mode processor 24. The echo signals from the volumetric region are processed to form a 3D image dataset by a 3D image processor as described more fully below. The 3D image data may be processed for display in several ways. One way is to produce multiple 2D planes of the volume. This is described in U.S. Pat. No. 6,443,896 (Detmer). Such planar images of a volumetric region are produced by a multi-planar reformatter 34. The three dimensional image data may also be rendered to form a perspective or kinetic parallax 3D display by a volume renderer 36. The resulting images, which may be B mode, Doppler or both as described in U.S. Pat. No. 5,720,291 (Schwartz), are coupled to a display processor 38, from which they are displayed on an image display 40. User control of the beamformer controller 22 and other functions of the ultrasound system are provided through a user interface or control panel 20.

Figure 2:
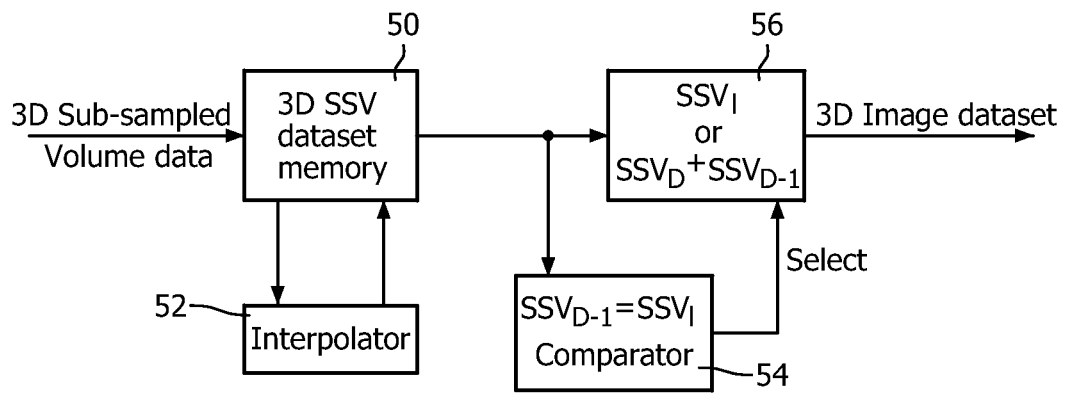
FIG. 2 illustrates the details of one implementation of the 3D image processor of FIG. 1 in block diagram form.

In order to provide 3D images which are highly resolved and free of sampling artifacts, the volumetric region being imaged must be spatially sampled with a beam density that satisfies the Nyquist criterion, as explained in U.S. patent application publication no. 2007/0123110 (Schwartz). Some implementations of the present invention will spatially sample a volume near or below the threshold of this spatial sampling criterion. The 3D data from such low density scanning of a volumetric region is referred to herein as 3D sub-sampled volume data. The 3D sub-sampled volume data may be B mode data, Doppler data, or a combination of the two. Such 3D sub-sampled volume datasets are coupled from the B mode processor 24 and/or the Doppler processor 30 to a memory device 50 as shown in FIG. 2. Since each sub-sampled volume dataset ($SSV_D$) is itself a sampling of the full volume to be imaged, albeit a sub-sampling, it can be processed to produce a 3D view of the full volume. In accordance with a first aspect of the present invention, this is done by an interpolator, which interpolates additional display values between the sampled (acquired) data points of the $SSV_D$. Various types of linear, nonlinear, and weighted interpolation can be used to interpolate these additional display values and an example is given below. The additional display values are incorporated into the acquired $SSV_D$ at their appropriate spatial positions between the acquired data points to produce an interpolated, sub-sampled volume dataset, $SSV_I$. Since the interpolation of the additional display values can be done in less time than the time required to acquire the $SSV_D$, the $SSV_I$ can be displayed at the acquisition frame rate of the $SSV_D$. The $SSV_I$ and the $SSV_D$ are stored in the dataset memory 50 for use as described below.

In accordance with a further aspect of the present invention, the ultrasonic imaging system determines whether to display an interpolated 3D dataset $SSV_I$, or a 3D dataset which is an interleaved combination of two or more 3D datasets. The ultrasound system does this by determining which dataset will produce the highest quality image. If the region being imaged is moving such as a rapidly beating heart, or the probe is being moved as the datasets are acquired, the motion will affect the image quality. The time interval between the acquisitions of two spatially different image data points in the same sub-sampled volume will be less than the time interval between two spatially adjacent image points acquired in different sub-sampled volume acquisitions. This means that interpolated display values between samples in the same sub-sampled volume will be less affected by motion than will spatially adjacent samples from two different sub-sampled volumes because the data values used for the interpolation will be acquired more closely in time. The samples from different, even consecutive, sub-sampled volumes will be more widely separated in time and hence more susceptible to motion distortion. Comparator 54 in FIG. 2 makes this determination. The comparator 54 compares a data point of a sub-sampled volume dataset acquired earlier in time, $SSV_{D-1}$, with a recently interpolated display value for the same spatial location in $SSV_I$. If there has been motion in the time interval between the time of the earlier 3D sub-sampled volume and the most recent one, the values for the same spatial location will be different. If there has been no motion over the time interval between the two volume acquisitions, the values for the same spatial location will be substantially the same. In the case where motion is present, the comparator selects use of the most recent interpolated sub-sampled volume, $SSV_I$. If there is no motion, then the acquired data values of the earlier acquired sub-volume are interleaved in their proper spatial locations of the most recently acquired sub-volume. Any unfilled spatial locations of the merged sub-volumes may be filled with interpolated values. The interleaved sub-volume has been found to present a more highly resolved 3D image when motion is not present.

The Select signal from the comparator 54 is coupled to a processor which selects either the interpolated sub-volume $SSV_I$ when motion is present, or interleaves the earlier acquired data points ($SSV_{D-1}$) with the recently acquired data points ($SSV_D$). The selected 3D image dataset is forwarded on for subsequent processing (e.g., volume rendering, display processing) and display.

Figure 3:
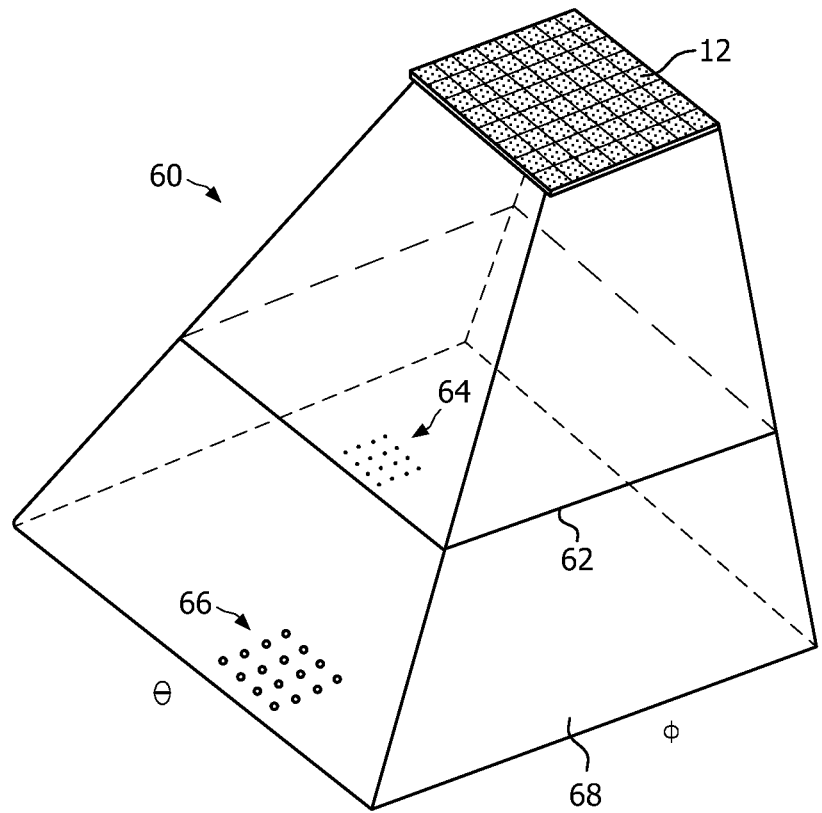
FIG. 3 illustrates a volumetric region which is being scanned by sub-sampling in accordance with the principles of the present invention.

FIG. 3 illustrates one implementation of the present invention. In this example a two dimensional array transducer 12 is transmitting and receiving beams which sub-sample a volumetric region 60 in front of the transducer array. The beams are electronically steered by the array so that they scan a volumetric region which in this example has the shape of a truncated pyramid. Other shapes such as conical shapes may also be employed. A pattern of dots 64 is shown where the beams pass through a C plane 62 which is parallel to the plane to the plane of the array transducer. At this intermediate depth in the volume the beams are seen to be relatively closely spaced in both azimuth ($\theta$) and in elevation ($\phi$). As the beams travel to the maximum depth 68 of the volumetric region 60, they diverge further in both azimuth and elevation as indicated by the pattern of dots 66. The spatial locations between beams in azimuth and elevation are where additional values for display are interpolated or interleaved. There is generally no need to add additional display point values in the depth dimension, as the sampling of returning echo signals is sufficiently high and produces high density sampling in the depth (axial) direction of the beams. It can be seen from FIG. 3 that the need for additional interspaced values for display is greatest at the greater depths when the beams diverge with depth as illustrated in FIG. 3.

FIG. 4a illustrates four different beam patterns in which the volumetric region 60 may be sub-sampled in accordance with the present invention. Each beam pattern is of the intersection of beams with an elevation plane such as plane 62 in FIG. 3. In this illustration an "X" indicates a spatial location where a beam is transmitted and received, and an "O" indicates a spatial location where a beam could be, but is not, transmitted and received. If the elevation plane were fully spatially sampled, each of the sixteen spatial locations would contain an "X". But in FIG. 4a, the spatial locations which are sub-sampled vary with each 3D scan of the volumetric region. In pattern P1, the first spatial location in the first and third rows is sampled and the other spatial locations in these rows are not sampled. In the second and fourth rows, the third spatial location is sampled and the other locations are not sampled.

In the other sampling patterns P2-P4, different spatial locations are sub-sampled. In P2 the fourth and second locations in successive rows are sampled. In P3 the third and first locations in successive rows are sampled. And in pattern P4 the second and fourth locations in successive rows are sampled. After the volumetric region has been scanned with these four patterns, each producing its own sub-sampled volume (SSV), it is seen that all spatial locations have been sampled once. The sequence of scanning patterns then repeats with subsequent scans of the volumetric region. It can also be seen that if the samples from the four patterns are interleaved or merged together, a fully sampled volume is produced. Interleaving the samples from all four patterns will produce one pattern in which all sixteen spatial locations comprises sampled (acquired) values, albeit acquired over four volume scan intervals. If there were no motion in the volume, the interleaving of the samples from the four patterns will produce a well resolved and undistorted volume image. When the sequence repeats, the next pattern which is scanned, a repeat of pattern P1, produces samples which are used to replace the samples from the earlier scan with pattern P1. In this way a portion (one-quarter in this example) of the volumetric data is updated with the new scan with each different pattern. After the four scans with the four patterns have been repeated, all of the sample values of the interleaved volume have been updated.

But if there is motion in the volumetric region during the time required to scan with the four patterns, an interleave of the four patterns will produce a poorly resolved or distorted image dataset. This problem is prevented by interleaving fewer than all four scans and filling in unsampled spatial locations with interpolated values. At a minimum, only a single pattern dataset is used with missing samples filled in by interpolation. FIG. 4b illustrates one way in which interpolation can be performed. The P1 sub-sampling pattern is shown on the left side of the drawing, with the acquired sub-samples denoted as $X_1$-$X_4$. One way to interpolate the missing "O" samples is to compute a value for $O_1$ from $X_1$ and $X_3$ by calculating $$O_1 = AVG\{X_1, X_3\}$$

The interpolated $O_1$ value is then used with the value of $X_2$ to compute a value for $O_2$ by $$O_2 = AVG\{O_1, X_2\}$$

Similarly, $X_2$ and $X_4$ are used to compute a value for $O_4$ by $$O_4 = AVG\{X_2, X_4\}$$

and $X_3$ and $O_4$ are used to compute a value for $O_3$ by $$O_3 = AVG\{X_3, O_4\}$$

The other missing values in the matrix of values are similarly filled in by interpolation and/or extrapolation.

The missing values in the P2 pattern on the right side of the drawing are likewise filled in by interpolation. $X_1$ and $X_3$ are used to compute a value for $O_1$; $O_1$ and $X_2$ are used to compute a value for $O_2$; $X_2$ and $X_4$ are used to compute a value for $O_3$; and $O_3$ and $X_3$ are used to compute a value for $O_4$.

When deciding whether to use an interpolated sub-sampled volume or an interleaved sub-sampled volume, a comparison is made of an actually acquired value and an interpolated value at the same spatial location. For instance, the interpolated $O_2$ value of the 3D dataset produced from pattern P1 is compared with the acquired value $X_2$ of the 3D dataset produced from pattern P2. If the values are substantially the same, this indicates that there has been no significant motion between the acquisition times of the two 3D datasets. Thus, the actually acquired samples $X_1$-$X_4$ of the pattern P2 dataset can be interleaved with the data values of the 3D dataset of pattern P1. In this example this is done by using the $X_1$ value of P2 for the value of $O_0$ in P1; using the $X_2$ value of P2 for the value of $O_2$ in P1; using the $X_3$ value of P2 for the value of $O_5$ in P1; and using the $X_4$ value of P2 for the value of $O_6$ in P1. Other acquired values from other 3D datasets acquired with the other patterns can be similarly interleaved if there has been no motion between the source and destination 3D datasets.

On the other hand, if the comparison of $X_2$ of the P2 dataset with the interpolated $O_2$ value of the P1 dataset shows a significant difference, then there has been motion between the times of acquisition of the two 3D datasets. In that case the P1 dataset with all "O" values being interpolated and/or extrapolated values would be used for display to minimize distortion and blurring in the 3D image.

In a constructed embodiment of the present invention, the decision of whether to use interpolated or interleaved data for the 3D display is not done on a global basis for the entire image, but on a pixel-by-pixel basis. A given ultrasound image may be expected to have motion in only a portion or certain regions of the image, and not over the entire image. For instance, if 3D imaging is being done of a fetus and the fetus is stationary during the time of imaging, most of the regions of the fetus in the display are not moving from one 3D frame to the next. Accordingly, the display points from these stationary regions, when compared, would indicate that display points can be interleaved from multiple 3D scans to produce a highly resolved image of those areas in the display. The fetal heart, however, is constantly beating and a comparison of display points from temporally discrete scans would indicate motion of the display points of the fetal heart. Thus, interpolation would be used to display the fetal heart region in an image, as the acquired data being used would all be from the same 3D scan and not from multiple, temporally discrete scans. The fetal heart would thus appear at its best quality, undistorted by motional effects, while the rest of the 3D image would be interleaved acquired data points from multiple successive scans. Each region of the 3D display is thereby optimized for the best image quality of display by determining on a display point-by-display point basis whether to use interpolated or interleaved display data at each point in the displayed volume.

Figures 5A, 5B, 6:
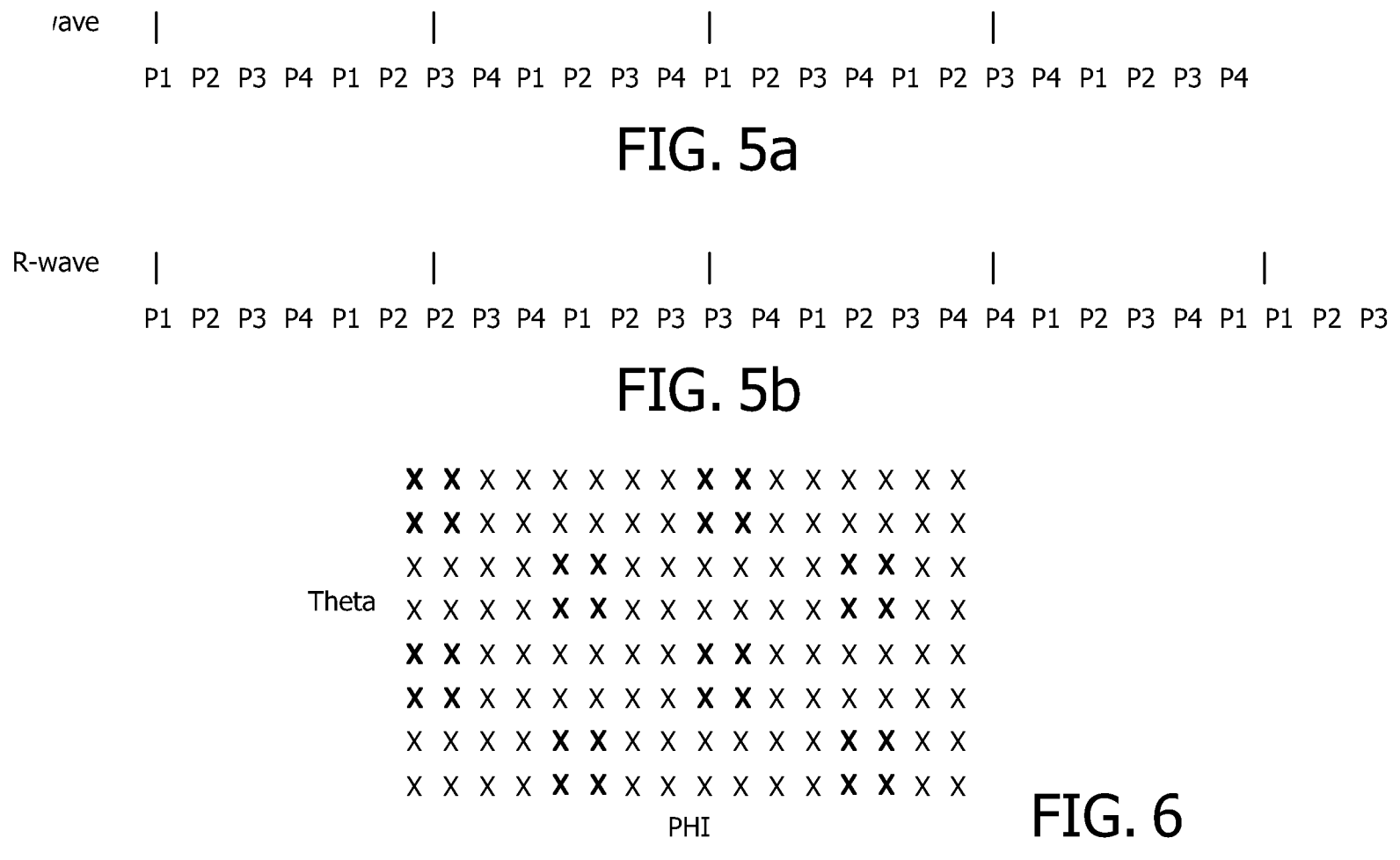

When the 3D display technique of the present invention is being used to image an organ with repetitive motion, such as the beating of the heart, the scan patterns can be either synchronous or asynchronous with respect to the motional cycle, in the case of the heart, the heartbeat. Asynchronous and synchronous scan patterns are illustrated in FIGS. 5a and 5b. In FIG. 5a the heart is imaged in 3D by four sequentially recurring scan patterns P1 through P4. Above the sequence of patterns are vertical lines marking the occurrence of each successive R-wave. The time between R-waves is the interval of one heartbeat. In this illustrative example a sparsely sampled volume dataset is acquired every one-sixth of a heart cycle; there are six acquisitions per heartbeat. After a sequence of patterns P1-P4 is used, the sequence repeats. Since the heart is constantly moving, consecutive dataset acquisitions are not interleaved, as the heart appears differently at each phase of the heart cycle. In that case, each sparse sampling pattern is filled in with interpolated values to display its particular phase of the heart cycle. If the scan patterns are acquired rapidly enough so that there is no significant motion during the acquisition of two or more consecutive scan patterns, the data points from those scan patterns could be interleaved. Moreover, it may be possible to combine data points from the same phase of different heart cycles if the heartbeat is regular and the heart follows the same motional path during each heartbeat. For instance, the pattern used for the first phase of the first heartbeat is a P1 pattern, and the pattern used for the first phase of the second heartbeat is a P3 pattern. For a regular heartbeat the comparison of interpolated and acquired values from these two acquisitions may indicate that the heart is in the same position at each of these first-phase acquisitions and hence the acquired data values from the first P1 pattern and the second P3 pattern can be interleaved. Other missing values can be interpolated. This would produce a higher quality image than simply using all interpolated values. Similarly, the acquired values of the P2 pattern at the second phase of the first heart cycle may be interleaved with the P4 data values of the second phase of the second heart cycle. Thus, the acquisition sequence of FIG. 5a, given repetitive heart motion, may be expected to be displayed as either entirely interpolated 3D images or two interleaved data patterns with the remaining data points being interpolated.

FIG. 5b illustrates a second pattern sequence, which is to start the acquisition of each heart cycle with the next pattern in the sequence. It is seen that the P1 pattern is used for the first phase of the first heart cycle, the P2 pattern for the first phase of the second heart cycle, the P3 pattern for the first phase of the third heart cycle, and the P4 pattern for the first phase of the fourth heart cycle. When the heart motion is repetitive, a full 3D dataset can be interleaved from the acquired data of these four different acquisition patterns. Each displayed 3D heart image of each heartbeat is composed entirely of acquired data values with no interpolation. A similar high quality image can be formed at each phase of the heart cycle. With the fifth heart cycle the P1 pattern data of the first heart cycle is replaced with an acquisition using the new P1 pattern data to update the image.

With each of the acquisition sequences of FIGS. 5a and 5b, the 3D image display rate is at the acquisition rate used to acquire each sparsely sampled volume P1-P4, regardless of whether interpolation or interleaving is used or a combination of the two. It will be appreciated that, while the examples given use four different scanline patterns P1-P4, a greater or lesser number of different scanline patterns may be used in a given implementation.

FIG. 6 illustrates a preferred implementation of the present invention, which benefits from the use of multiline acquisition. As is known, multiline enables the reception of data from multiple scanlines during a single transmit-receive interval. In FIG. 6 the Xs shown in bold represent four scanlines acquired with 4× multiline. The Xs which are not in bold indicates a spatial location where acquisition is not done in the displayed pattern. In this example, a beam is transmitted to insonify each group of four adjacent scanlines, and the echo data from all four scanlines is received simultaneously. A multiline beamformer 18 then processes and produces four adjacent scanlines simultaneously. See, for example, U.S. Pat. No. 6,482,157 (Robinson). Instead of insonifying adjacent scanlines with one transmit beam, four differently directed, simultaneously transmitted, transmit beams can be used to simultaneously insonify and received four differently located scanlines as described, for instance, in U.S. Pat. No. 7,537,567 (Jago et al.). FIG. 6 illustrates a multiline implementation of the P1 pattern, in which a group of four adjacent scanlines is acquired, then three groups of four are skipped before another multiline acquisition of four scanlines is performed. With 4× multiline, the 3D dataset can be acquired in one-quarter of the time to do the same without multiline, thereby increasing the frame rate of display by a factor of four. As in the examples of FIGS. 4a and 4b, different multiline patterns can be sequentially used to perform different sparse sub-samplings of a volumetric region, then the data values interleaved or interpolated or both to produce a new image for display at the volume acquisition rate.

What is claimed is:

1. A 3D ultrasonic diagnostic imaging system for high frame rate 3D cardiac display comprising:
   an ultrasound probe having an array transducer adapted to sub-sample a volumetric region and acquire received scanlines which are separated in both azimuth and elevation directions;
   a beamformer coupled to the ultrasound probe which produces image data values along the scanlines;
   a beamformer controller, coupled to the beamformer, adapted to scan the heart with a repetitive sequence of spatially different scanline patterns during different cardiac phases in which the full volumetric region is sub-sampled by each pattern, wherein the different scanline patterns each include different locations of transmit and receive beams within an array of possible positions for transmit and receive beams during scanning, and wherein positions of the transmit and receive beams in the scanline patterns used during successive heartbeats for each comparable cardiac phase is changed such that over a period of N heartbeats the same cardiac phase of each heartbeat is scanned with N different scanline patterns such that each position in the array of possible positions is sampled;
   a 3D image processor, responsive to the image data values from different cardiac phases, and adapted to fill spatial locations between received scanlines with interpolated or interleaved data values, wherein the 3D image processor comprises a comparator adapted to compare data values from different cardiac phases to determine whether to fill the spatial locations between received scanlines with interpolated data values from the same cardiac phase or interleaved data values from another cardiac phase, wherein the comparator is further adapted to compare an interpolated data value of a 3D dataset acquired during one cardiac phase with a spatially corresponding received data value of a 3D dataset acquired during a different cardiac phase, wherein a determination by the comparator that the compared interpolated and received data values are different causes the 3D image processor to produce a 3D image dataset of interpolated data values, and wherein a determination by the comparator that the compared interpolated and received data values are equal causes the 3D image processor to produce a 3D image dataset of interleaved data values from a plurality of different cardiac phases; and a display, coupled to the 3D image processor, adapted to display a 3D image of interpolated data values, interleaved data values, or both, wherein the 3D image processor causes the display to display a new 3D cardiac image at a frame rate of the scanline patterns.

2. The 3D ultrasonic diagnostic imaging system of claim 1, wherein the array transducer further comprises an electronically steered two dimensional array of transducer elements.

3. The 3D ultrasonic diagnostic imaging system of claim 1, wherein the determination by the comparator is done on a pixel by pixel basis.

4. The 3D ultrasonic diagnostic imaging system of claim 1, wherein the different scanline patterns further comprise spatially different scanning patterns in which beams are transmitted along a first set of beam directions and omitted from other beam directions in one scanning pattern, and beams are transmitted along a second, different set of beam directions and omitted from other beam directions in another scanning pattern.

5. The 3D ultrasonic diagnostic imaging system of claim 1, wherein the 3D image processor further comprises a motion detector adapted to detect the presence of motion between different cardiac phases to determine whether to fill the spatial locations between received scanlines with interpolated or interleaved data values.

6. The 3D ultrasonic diagnostic imaging system of claim 1, wherein the 3D image processor is adapted to interleave the data values from N successive scanline patterns of the same cardiac phase over N heartbeats.

7. The 3D ultrasonic diagnostic imaging system of claim 6, wherein N is at least four, and the 3D image processor is adapted to interleave the data values from the at least four different successive scanline patterns used during the same cardiac phase of at least four successive heartbeats.

8. The 3D ultrasonic diagnostic imaging system of claim 1, wherein the 3D image processor is adapted to determine whether to fill spatial locations between received scanlines with interpolated or interleaved data values on a pixel by pixel basis.

9. The 3D ultrasonic diagnostic imaging system of claim 1, wherein the beamformer further comprises a multiline beamformer.

10. The 3D ultrasonic diagnostic imaging system of claim 9, wherein the multiline beamformer is adapted to simultaneously receive echo signals from a group of adjacent scanlines, wherein the beamformer controller is adapted to subsample the volumetric region by omitting echo acquisition from at least one group of adjacent scanlines which is between groups from which echo signals are received.

11. The 3D ultrasonic diagnostic imaging system of claim 1, wherein the 3D image processor is configured to produce a 3D image of the full volumetric region from a single scan line pattern.

12. The 3D ultrasounic diagnostic imaging system of claim 1, wherein the different scanline patterns spatially sample the volumetric region at or below a Nyquist criterion.

* * * * *